United States Patent [19]

Takeuchi

[11] Patent Number: 4,526,998

[45] Date of Patent: Jul. 2, 1985

[54] DEODORIZED FORMALIN

[76] Inventor: Naoyuki Takeuchi, 1876-258 Tantakabayashi, Sumiyoshi-cho, Higa-shinada-ku, Kobe, Hyogo, Japan

[21] Appl. No.: 641,695

[22] Filed: Aug. 17, 1984

[30] Foreign Application Priority Data

Aug. 18, 1983 [JP] Japan .................. 58-152255

[51] Int. Cl.³ .............................................. C07C 45/86
[52] U.S. Cl. ...................................... 568/422; 568/421
[58] Field of Search ................................ 568/421, 422

[56] References Cited

U.S. PATENT DOCUMENTS

| 3,137,736 | 6/1964 | Prinz et al. | 568/422 |
| 3,379,769 | 4/1968 | Prinz et al. | 568/422 |
| 3,532,756 | 10/1970 | Prinz et al. | 568/422 |
| 3,658,912 | 4/1972 | Wambach et al. | 568/422 |
| 3,816,539 | 6/1974 | Sanborn et al. | 568/422 |
| 4,085,079 | 4/1978 | Kmetz et al. | 568/422 |
| 4,247,487 | 1/1981 | Percy | 568/422 |

FOREIGN PATENT DOCUMENTS

| 4109 | 6/1977 | Japan | 568/422 |
| 73811 | 6/1982 | Japan | 568/422 |
| 1187328 | 4/1970 | United Kingdom | 568/422 |

Primary Examiner—Werren B. Lone

[57] ABSTRACT

Deodorized formalin produced by mixing formalin with additives comprising methyl salicylate and ethanol or methanol. A desired mixing ratio of these components is required.

9 Claims, No Drawings

DEODORIZED FORMALIN

The present invention relates to the deodorization of formalin while the deodorized formalin retains performances of disinfection and preservation, which are characteristic of formalin.

Formalin can generally be used as an industrial raw material to produce a variety of useful synthetic resins by reaction with different organic materials, for instance, phenol, urea, melanine, etc.

Formalin can also be applied to the fields of medical treatment and sanitation as a disinfectant and as a preservative. In use, objects to be disinfected or preserved can be immersed in, or sprayed by, formalin in the form of a liquid, or they can be placed in a vaporized formalin gas. Formalin has a particularly and highly offensive smell when it is used in the form of a gas.

The present invention is intended to eliminate such odour from formalin on the market.

The object of the present invention is to provide a novel reagent referred to as deodorized formalin, in which the above-mentioned smell has been removed from formalin while retaining the qualities of disinfection and preservation which are characteristic of formalin.

Deodorized formalin of the present invention can be produced by mixing formalin with additives comprising methyl salicylate and ethanol or methanol, and completely dissolving these additives in the formalin.

Experiments showed that it is most preferable that a product of the present invention has a mixing ratio of 9.9 ml of pharmacopocial formalin, 0.1 ml of methyl salicylate and 0.7 to 0.8 ml of pharmacopoeial ethanol.

For a better understanding of the invention, the following description will be given based on experiments carried out with reference to various amounts of pharmacopoeial formation and the additives applied thereto; methyl salicylate, ethanol and methanol.

The following Tables 1, 2, and 3 show the quantitative relation between pharmacopocial formalin and such additives comprising products of a variety of mixing ratios.

In the table.

x: indicate that isolation of a large amount of methyl salicylate was observed. (The mixture turns an opaque white).

Δ: indicates that isolation of a very small amount of methyl salicylate was observed.

○: indicates that methyl salicylate has been fully dissolved.

TABLE 1

| Methyl salicylate (ml) | Formalin (ml) | Pharacopoeial ethanol (ml) | | | |
|---|---|---|---|---|---|
| | | 0.3 | 0.5 | 0.7 | 0.8 |
| 0.5 | 0.5 | x | x | x | x |
| 0.1 | 0.4 | x | | | |
| 0.1 | 0.9 | x | x | Δ | |
| 0.1 | 0.9 | x | x | x | |
| 0.1 | 9.9 | x | x | Δ | ○ (A) |

TABLE 2

| Methyl salicylate (ml) | Formalin (ml) | Pharacopoeial ethanol (ml) | | | |
|---|---|---|---|---|---|
| | | 0.3 | 0.5 | 0.6 | 0.7 |
| 0.4 | 0.1 | x | x | | |
| 0.9 | 0.1 | x | x | | |
| 1.9 | 0.1 | x | x | x | |

TABLE 3

| Methyl salicylate (ml) | Formalin (ml) | Pharacopoeial methanol (ml) | | | | |
|---|---|---|---|---|---|---|
| | | 0.5 | 0.6 | 0.8 | 0.9 | 1.0 |
| 0.1 | 0.4 | x | ○ | | ○ | |
| 0.1 | 0.9 | x | x | ○ (B) | (B) | |
| 0.1 | 1.9 | x | x | x | x | x |
| 0.1 | 0.6 | x | x | ○ | | |
| 0.1 | 9.9 | x | x | x | Δ (C) | (C) |
| 0.1 | 3.2 | x | x | x | x | x |

Each experiment listed in the table was carried out on the condition that the experimental products should retain a superior ability to fix cells, i.e. disinfect and preserve qualities which are characteristic of formalin, without being influenced by the additives.

In order to obtain maximum results, the mixing ratio of additives to formalin should be as small as possible. From this point of view, it will be readily understood that the product marked (A) in Table 1 is most preferable, and the products marked (B) and (C) in Table 3 are less preferable.

In this connection, it should be noted that the more fully methyl salicylate is dissolved, the greater the deodorizing effect, and that the deodorizing effects obtained by the products marked ○ and Δ in the tables are substantially the same.

However, both the chemical change which should have taken place with the above-described mixtures and a theory or mechanism by which such deodorized formalin should be produced are still unknown, but now under study.

In describing the present invention, reference has been made to preferred embodiments. In this regard, those skilled in the art and familiar with the disclosure of the subject invention will recognize that additions, deletions, substitutions, and/or changes may be made which will fall within the perview of the invention as defined in the following claims.

What is claimed is:

1. Deodorized formalin produced by mixing formalin with additives comprising methyl salicylate and ethanol and completely dissolving the additives therein.

2. Deodorized formalin as recited in claim 1 wherein said methyl salicylate is present in an amount of at least 0.9 vol %.

3. Deodorized formalin as recited in claim 1 wherein said ethanol is present in an amount of at least 6.0%.

4. Deodorized formalin produced by mixing formalin with additives comprising methyl salicylate and methanol, and completely dissolving the additives.

5. Deodorized formalin as recited in claim 4 wherein said methyl salicylate is present in an amount of at least 0.9 vol %.

6. Deodorized formalin as recited in claim 4 wherein said methanol is present in an amount of at least 8.0 vol %.

7. Deodorized formalin as recited in claim 1, wherein the mixing ratio is such that 0.1 ml of methyl salicylate and 0.7 to 0.8 ml of pharmacopoeial ethanol are mixed with 9.9 ml of pharmacopoeial formalin.

8. Deodorized formalin as recited in claim 4, wherein the mixing ratio is such that 0.1 of methyl salicylate and 0.9 to 1.0 ml of pharmacopoeial methanol are mixed with 9.9 ml of pharmacopoeial formalin.

9. Deodorized formalin as recited in claim 4, wherein the mixing ratio is such that 0.1 ml of methyl salicylate and 0.8 to 0.9 ml of pharmacopoeial methanol are mixed with 0.9 ml of pharmacopoeial formalin.

* * * * *